United States Patent [19]

Borror et al.

[11] 4,348,529
[45] Sep. 7, 1982

[54] SYNTHESIS OF CYCLIC DISULFONE COMPOUNDS

[75] Inventors: Alan L. Borror, Lexington; Ernest W. Ellis, Carlisle; Charles E. Hammond, Burlington, all of Mass.

[73] Assignee: Polaroid Corporation, Cambridge, Mass.

[21] Appl. No.: 294,408

[22] Filed: Aug. 19, 1981

[51] Int. Cl.³ .................. C07D 339/00; C07D 339/06; C07D 339/08
[52] U.S. Cl. .................................. 549/22; 542/441; 549/11; 549/35
[58] Field of Search ........................... 549/11, 21, 35; 542/441

[56] References Cited

PUBLICATIONS

Seebach et al., J. Org. Chem., vol. 40 (1975), pp. 231–237.
Corey et al., Tetra. Lett., vol. 33 (1967), pp. 3201–3204.

*Primary Examiner*—Richard Raymond
*Attorney, Agent, or Firm*—Sybil A. Campbell

[57] ABSTRACT

This invention relates to a method of synthesizing bis-sulfones of the formula

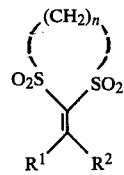

wherein $R^1$ and $R^2$ each are hydrogen, alkyl, phenalkyl, phenyl or phenyl-substituted with an electron-donating or electron-withdrawing group and n is an integer 2, 3 or 4 (a) by reacting a 1,3-dithio compound with n-butyllithium to generate the anion of said compound, (b) reacting said anion with a carbonyl compound to give the 2-substituted carbonol anion intermediate, (c) reacting said intermediate with an acyl chloride or a chloroformate to give the corresponding ester, and (d) reacting said ester with a peracid to give the bis-sulfone product. The subject invention also is concerned with the novel intermediates of step (c).

8 Claims, No Drawings

SYNTHESIS OF CYCLIC DISULFONE COMPOUNDS

BACKGROUND OF THE INVENTION

1. Field of the Invention

This invention relates to a method of synthesizing certain bis-sulfones and to intermediates useful in the preparation thereof.

2. Description of the Prior Art

The synthesis of 2-lithio-1,3-dithianes by reacting a dithiane with n-butyllithium in tetrahydrofuran (THF) at −20° C. is described by D. Seebach and E. J. Corey, J. Org. Chem., 1975, 40, p. 231. These authors also report the reaction of 2-lithio-1,3-dithianes with aldehydes, ketones, carboxylic acid derivatives and various other common electrophiles in THF at −20° to −70° C. The dehydration of certain of the resulting ketone and aldehyde adducts with, for example, p-toluenesulfonic acid to give the ketene thioacetals, i.e., the alkylidenedithianes also is described. The oxidation of alkylidenedithianes with m-chloroperbenzoic acid to give the corresponding bis-sulfones is reported by E. J. Corey and G. Märkl, Tetrahedron Letters, 1967, p. 3201.

The present invention is concerned with a method of synthesizing these bis-sulfones which employs a blocked intermediate.

SUMMARY OF THE INVENTION

It is, therefore, the primary object of the present invention to provide a method of synthesizing certain bis-sulfones.

It is another object of the present invention to provide intermediates useful in the synthesis of said bis-sulfones.

Other objects of this invention will in part be obvious and will in part appear hereinafter.

This invention accordingly comprises the processes involving the several steps and the relation and order of one or more of such steps with respect to each of the others, and the products possessing the features, properties and the relation of elements which are exemplified in the following detailed disclosure and the scope of the application of which will be indicated in the claims.

For a fuller understanding of the nature and objects of the present invention reference should be had to the following detailed description.

DESCRIPTION OF THE PREFERRED EMBODIMENTS

According to the present invention, certain bis-sulfones are prepared by reacting a 1,3-dithio compound,

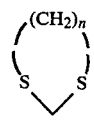

wherein n is an integer 2, 3 or 4 with n-butyllithium in tetrahydrofuran to generate the anion of said 1,3-dithio compound; adding to said anion a carbonyl compound

wherein $R^1$ and $R^2$ each are hydrogen, alkyl, phenalkyl, phenyl or phenyl-substituted with an electron-donating group or an electron-withdrawing group to give the 2-substituted carbonol anion intermediate:

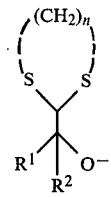

wherein $R^1$, $R^2$ and n have the same meaning given above; reacting said intermediate with a chloroformate or acyl chloride to give the corresponding ester:

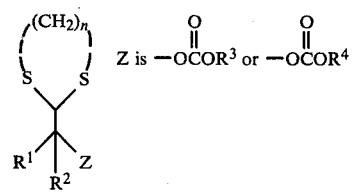

wherein $R^3$ is benzyl or ethyl, $R^4$ is methyl or phenyl and $R^1$, $R^2$ and n have the same meaning given above; and reacting said ester with a peracid to give the bis-sulfone having the formula:

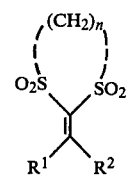

wherein $R^1$, $R^2$ and n have the same meaning given above.

The reaction scheme of the present method is illustrated below employing 1,3-dithiane as the starting 1,3-dithio compound:

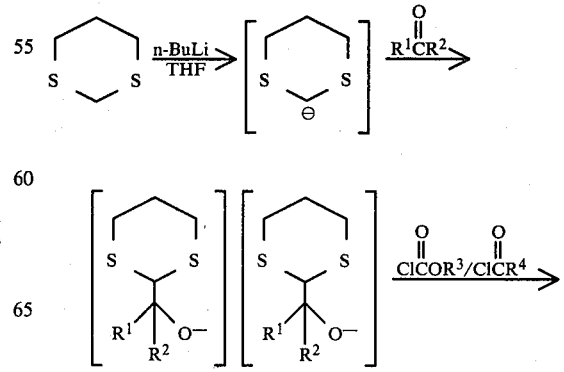

-continued

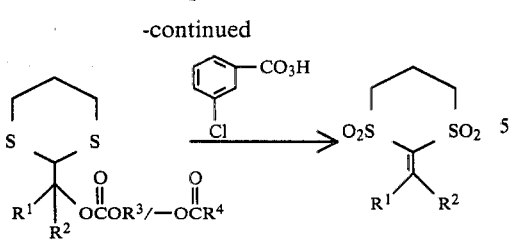

wherein $R^1$, $R^2$, $R^3$ and $R^4$ have the same meaning given above.

The novel intermediates of the present invention may be represented by the formula:

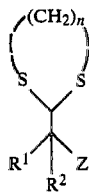

wherein Z is

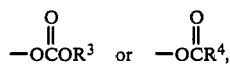

$R^1$ and $R^2$, the same or different, each are hydrogen, alkyl usually having 1 to 20 carbon atoms, phenalkyl wherein said alkyl usually has 1 to 20 carbon atoms, phenyl, or phenyl substituted with an electron-donating or electron-withdrawing group; $R^3$ is benzyl or ethyl; $R^4$ is methyl or phenyl; and n is an integer 2, 3 or 4.

In carrying out the subject method, the 1,3-dithio compound and n-butyllithium generally are used in equivalent amounts. This reaction to generate the anion of the dithio compound may be conducted over a relatively wide temperature range of between about 0° C. and −70° C. and usually is conducted at a temperature between about −30° and −70° C. The carbonyl compound is added to the above reaction solution at a temperature of about −30° C., and the reaction mixture may then be warmed to room temperature. The carbonyl compound and anion are reacted in equivalent amounts, and the resulting 2-substituted carbonol anion intermediate is then blocked as an ester by reacting 1 to 1.5 equivalents of an acyl chloride or a chloroformate, e.g., acetylchloride or benzylchloroformate to give the corresponding ester intermediate. The acyl chloride or chloroformate is added to the 2-substituted carbonol anion at about −30° C. followed by warming the reaction mixture to room temperature. A solution of the resulting ester in chloroform is then treated with about 4 to 8 equivalents of a peracid, preferably, m-chloroperoxybenzoic acid at about −20° C. to −40° C., and then is warmed to about 25° to 60° C. For example, the reaction mixture is allowed to come to room temperature, and in some cases refluxed, until oxidation is complete.

In the subject method it was quite unexpected that the ester group was eliminated concomitantly under the oxidation conditions leading to the bis-sulfone product.

The 1,3-dithio compounds used as starting materials in the subject method are known in the art, and if not available commercially, may be synthesized in a conventional manner from aldehydes (or acetals) and dithiols. The carbonyl compounds also may be synthesized if not commercially available. In the carbonyl compounds,

$R^1$ and $R^2$, the same or different, each are hydrogen, alkyl usually having 1 to 20 carbon atoms, phenalkyl wherein said alkyl usually has 1 to 20 carbon atoms, phenyl, or phenyl substituted with an electron-donating group or electron-withdrawing group. The chloroformates,

wherein $R^3$ is benzyl or ethyl and the acyl chlorides,

wherein $R^4$ is methyl or phenyl also are known and readily available.

By electron-donating group is intended "a group with a negative sigma value as defined by Hammett's Equation" and by electron-withdrawing group is intended "a group with a positive sigma value as defined by Hammett's Equation".

The alkyl groups comprising $R^1$ and $R^2$ and the alkyl portion of the phenalkyl groups comprising said $R^1$ and $R^2$ may be straight- or branched-chain alkyl, for example, methyl, ethyl, isopropyl, isobutyl, n-butyl, dodecyl, hexadecyl, etc. The electron-donating and electron-withdrawing groups may be substituted in the o-, m- or p-position of said phenyl ring. The electron-donating group usually has a negative sigma value of not more than about −0.84, and the electron-withdrawing group usually has a positive sigma value of not more than about 0.93. Examples of useful electron-donating groups include lower alkyl containing 1 to 6 carbon atoms, RO— wherein R is alkyl containing 1 to 20 carbon atoms, $C_6H_5O$—, and —NHR' wherein R' is hydrogen or a substituent such as alkyl having 1 to 20 carbon atoms or phenyl. Examples of useful electron-withdrawing groups include F, Cl, Br, I, $CF_3$, $CH_3SO_2$,

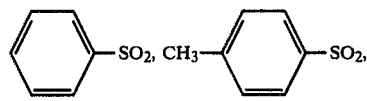

$CH_2Cl$, CN, $SO_3^-$, $SO_2NHR'$, $CONHR'$, $COOC_2H_5$, $COCH_3$, $NO_2$ and $SO_2CF_3$ wherein the R' of said sulfonamido and carboxamido groups has the same meaning given above.

The following examples are given to further illustrate the present invention and are not intended to limit the scope thereof.

EXAMPLE 1

Preparation of the compound having the formula:

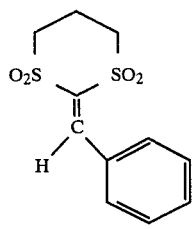

6.01 g of 1,3-Dithiane was dissolved in 250 ml of dry tetrahydrofuran (THF) at room temperature. This solution was cooled to −70° C. and 22 ml of 2.4 M n-butyllithium in hexane was added dropwise. The reaction mixture was allowed to stir at −40° to −15° C. for 2 hours and then cooled to −60° to −70° C. 5.1 ml of Benzaldehyde was added dropwise and the temperature was allowed to come to 0° C. The reaction mixture was then cooled back to −40° C. and 7.5 ml of benzylchloroformate was added dropwise. After stirring at room temperature overnight, the reaction mixture was diluted with ether to approximately 400 ml, filtered into a separatory funnel, washed with water (2×100 ml), dried over sodium sulfate, filtered and the solvent removed leaving a light yellow oil. The oil was placed under high vacuum overnight at room temperature. (A small cluster of white crystals in the oil was observed.) 250 ml of Ethanol was added to the oil and the mixture was stirred at 45°–50° C. for one and one-half hours, then allowed to come to room temperature. The white crystals were collected by filtration, washed with ethanol and air-dried to give 11.6 g of the intermediate having the formula:

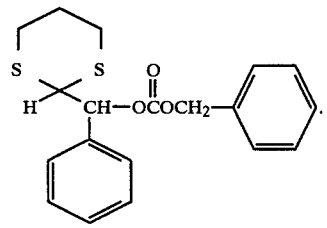

The intermediate prepared above (336 mg) was dissolved in 5 cc of chloroform and the resulting solution cooled to −20° C. To this solution was added a suspension of 794 mg of m-chloroperoxybenzoic acid in 5 ml of chloroform and the mixture was allowed to come to room temperature overnight under nitrogen. The solution was diluted with chloroform and washed with pH 7.5 buffer then with water, dried over sodium sulfate, filtered and the solvent removed to leave the title compound as crystals which were dried under high vacuum.

EXAMPLE 2

Preparation of the compound having the formula:

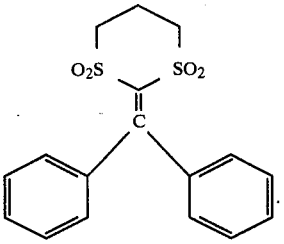

1,3-Dithiane (0.1 mol) was dissolved in 250 ml of dry THF. This solution was cooled to −30° C. and 46 ml of 2.4 M n-butyllithium (approx. 0.1 mol) was added dropwise over 20 minutes. After stirring at −30° C. or below for about one hour, a solution of benzophenone (0.1 mol) in 40 ml dry THF was added dropwise to the reaction mixture at −30° C. over 45 minutes. The resulting mixture was stirred for one and one-half hours at −30° C., then benzylchloroformate was added at −30° C. over 10 minutes. The mixture was allowed to come to room temperature overnight and another 10 ml of benzylchloroformate was added to force the reaction to completion. After stirring at room temperature for several hours, TLC showed one new compound. The carbonate ester intermediate was collected by filtration to give 32 g of said intermediate having the formula:

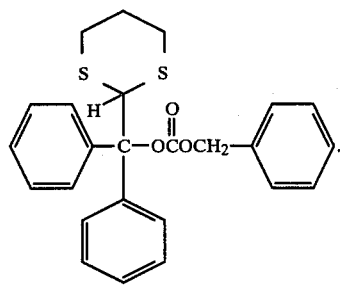

m-Chloroperoxybenzoic acid (12 g) was dissolved in approximately 200 ml of chloroform and the solution cooled to −25° C. The intermediate prepared above (5 g) was added to the solution all at once, and the reaction mixture was allowed to come to room temperature while stirring. After about two and one-half hours at room temperature the solids, m-chlorobenzoic acid, were collected by filtration. The filtrate was cooled to −50° C. and more m-chlorobenzoic acid collected. Again, the filtrate was cooled to −50° C. and the solids collected a third time. The third crop of solids filtered at −50° C. also contained a very small amount of desired product. The filtrate was then concentrated under vacuum to give 5.7 g of a white solid which was crystallized from warm acetone. High pressure liquid chromatography of 4.5 g of this solid using methylene chloride as eluant gave 1.5 g of the title compound which was purified further by recrystallization from methanol.

EXAMPLES 3–6

Preparation of the compounds having the formulae:

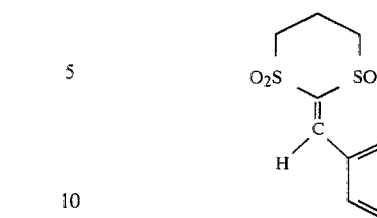

| Example | R¹ | R² |
|---|---|---|
| 3 | —H | —C₆H₄—OCH₃ |
| 4 | —H | —C₆H₄—CH₃ |
| 5 | —H | —C₆H₄—Cl |
| 6 | —H | —C₆H₄—SO₂CH₃ |

The compounds of Examples 3 to 6 were synthesized in the same manner as the compound of Example 2 by dissolving one equivalent of 1,3-dithiane in dry THF, cooling the solution to about −30° C., slowly adding about one equivalent of 2.4 M n-butyllithium to generate the dithiane anion and then slowly adding about one equivalent of the selected aldehyde also at about −30° C. The 2-substituted dithiane carbonol anion intermediate was then reacted with benzylchloroformate at −30° to −40° C. to give the carbonate ester intermediate which was converted to the final product by treating with four to eight equivalents of m-chloroperoxybenzoic acid at −20° to −40° C. in dry chloroform and warming to room temperature.

The elemental analyses for the compounds prepared in Examples 1 to 4 and the elemental analysis for the carbonate ester precursor to the compound prepared in Example 6 are set forth below.

| Ex. No. | Calculated | | | Found | | |
|---|---|---|---|---|---|---|
| | C | H | S | C | H | S |
| 1 | 48.51 | 4.44 | 23.54 | 48.49 | 4.40 | 23.64 |
| 2 | 58.60 | 4.59 | 18.40 | 58.39 | 4.57 | 18.22 |
| 3 | 47.67 | 4.66 | 21.22 | 47.74 | 4.67 | 21.03 |
| 4 | 55.33 | 4.93 | 22.39 | 50.25 | 4.93 | 22.24 |
| 6* | 59.08 | 5.40 | 23.66 | 58.92 | 5.40 | 23.62 |

*Analysis for the carbonate ester having the formula

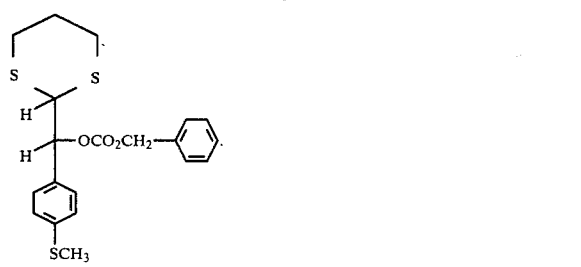

EXAMPLE 7

Preparation of the compound having the formula:

The compound of Example 7 was prepared in substantially the same manner as described in Example 2 except that the 2-substituted dithiane carbonol anion intermediate was reacted with 1.1 equivalents of acetylchloride to give the acetate ester intermediate which was then converted to the final product by treating with 4 equivalents of m-chloroperoxybenzoic acid.

The bis-sulfones produced by the subject method release the cyclic bis-sulfone portion of the molecule in aqueous alkali. Since the cyclic bis-sulfones released function as photographic silver halide solvents, the compounds produced by the subject method find utility in photographic products and processes for releasing a given amount of silver halide solvent at a given location in the film unit at a given time during processing. Their use in photography as silver halide solvent precursors is disclosed and claimed in copending U.S. Patent Application Ser. No. 294,311 of Alan L. Borror and Ernest W. Ellis filed concurrently herewith.

Since certain changes may be made in the herein-described subject matter without departing from the scope of the invention herein involved, it is intended that all matter contained in the above description and examples be interpreted as illustrative and not in a limiting sense.

What is claimed is:

1. A method of synthesizing bis-sulfones which comprises (a) reacting a 1,3-dithio compound, $$\begin{array}{c} (CH_2)_n \\ S \quad S \end{array}$$

wherein n is an integer 2, 3 or 4 with n-butyllithium in tetrahydrofuran to generate the anion of said 1,3-dithio compound;

(b) adding to said anion a carbonyl compound $$R^1\overset{O}{\underset{\|}{C}}R^2$$

wherein R¹ and R² each are hydrogen, alkyl, phenalkyl, phenyl or phenyl-substituted with an electron-donating group or an electron-withdrawing group to give the 2-substituted carbonol anion intermediate:

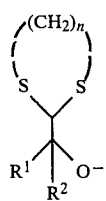

wherein $R^1$, $R^2$ and n have the same meaning given above;

(c) reacting said intermediate with a chloroformate or acyl chloride to give the corresponding ester:

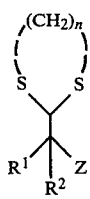

wherein Z is

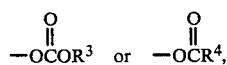

$R^3$ is benzyl or ethyl; $R^4$ is methyl or phenyl; and $R^1$, $R^2$ and n have the same meaning given above; and (d) reacting said ester with a peracid to give the bissulfone having the formula

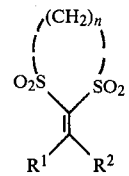

wherein $R^1$, $R^2$ and n have the same meaning given above.

2. A method as defined in claim 1 wherein said n is 3.
3. A method as defined in claim 1 wherein said $R^1$ is hydrogen.
4. A method as defined in claim 3 wherein said $R^2$ is phenyl-substituted with an electron-donating group.
5. A method as defined in claim 3 wherein said $R^2$ is phenyl-substituted with an electron-withdrawing group.
6. A method as defined in claim 1 wherein said acyl chloride is acetyl-chloride.
7. A method as defined in claim 1 wherein said chloroformate is benzylchloroformate.
8. A method as defined in claim 1 wherein said peracid is m-chloroperoxybenzoic acid.

* * * * *